US007402281B2

United States Patent
Huynh-Ba et al.

(10) Patent No.: US 7,402,281 B2
(45) Date of Patent: Jul. 22, 2008

(54) MAGAZINE FOR INVENTORYING REACTION CUVETTES IN AN AUTOMATIC ANALYZER

(75) Inventors: Thai Huynh-Ba, Newark, DE (US); William Jackson Devlin, Sr., Lincoln University, PA (US); Daniel Bernard Eichinger, New London, PA (US); Timothy Patrick Evers, Wilmington, DE (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 178 days.

(21) Appl. No.: 10/622,435

(22) Filed: Jul. 18, 2003

(65) Prior Publication Data

US 2005/0013747 A1     Jan. 20, 2005

(51) Int. Cl.
*B01N 21/13*     (2006.01)
(52) U.S. Cl. .......................... 422/63; 422/64; 422/104
(58) Field of Classification Search ................ 422/63, 422/99, 102, 64, 104; 206/503, 504, 509; 436/45; 221/68, 92, 83, 85, 151, 154
See application file for complete search history.

(56) References Cited

U.S. PATENT DOCUMENTS

| | | | |
|---|---|---|---|
| 4,634,575 A | 1/1987 | Kawakami et al. ............. 422/63 |
| 4,636,477 A | 1/1987 | Ronka et al. ................... 436/48 |
| 4,675,299 A | 6/1987 | Witty et al. ................... 436/165 |
| 5,048,957 A | 9/1991 | Berthold et al. ............. 356/246 |
| 5,055,262 A | 10/1991 | Sakagami ..................... 422/64 |
| 5,096,672 A | 3/1992 | Tervamaki et al. .......... 422/102 |
| 5,250,440 A | 10/1993 | Kellen et al. .................. 436/48 |
| 5,251,778 A | 10/1993 | Eggl .......................... 220/526 |
| 5,292,484 A | 3/1994 | Kelln et al. ................. 422/102 |
| 5,314,825 A | 5/1994 | Weyrauch et al. | |
| 5,332,549 A * | 7/1994 | MacIndoe, Jr. ............... 422/63 |
| 5,536,472 A * | 7/1996 | Terashima et al. ............. 422/63 |
| 5,921,435 A * | 7/1999 | Billet ......................... 221/185 |
| 6,098,819 A * | 8/2000 | Link ........................ 211/85.13 |
| 6,321,609 B1 * | 11/2001 | Mengel et al. ........... 73/863.21 |
| 6,328,164 B1 | 12/2001 | Riekkinen et al. ........... 206/569 |
| 6,752,967 B2 * | 6/2004 | Farina et al. ................ 422/102 |
| 2003/0032171 A1 * | 2/2003 | Gemmell et al. ......... 435/286.2 |

FOREIGN PATENT DOCUMENTS

WO     WO 00/44498 A1     8/2000

* cited by examiner

*Primary Examiner*—Jill Warden
*Assistant Examiner*—Natalia Levkovich
(74) *Attorney, Agent, or Firm*—Leland K. Jordan

(57) ABSTRACT

A magazine for releasably inventorying a plurality of reaction cuvettes to be used in an automatic clinical analyzer, the magazine comprising a generally rectangular storage cell having curved front and back surfaces, and a number of storage chutes therein, each chute sized to hold reaction cuvettes stacked one atop another therein.

4 Claims, 16 Drawing Sheets

US 7,402,281 B2

MAGAZINE FOR INVENTORYING REACTION CUVETTES IN AN AUTOMATIC ANALYZER

FIELD OF THE INVENTION

The present invention relates to an apparatus for automatically analyzing a patient's biological fluids such as urine, blood serum, plasma, cerebrospinal fluid and the like. In particular, the present invention provides a magazine with security features and a moveable closure for releasably inventorying a reaction cuvette in the analyzing apparatus.

BACKGROUND OF THE INVENTION

Various types of tests related to patient diagnosis and therapy can be performed by analysis assays of a sample of a patient's infections, bodily fluids or abscesses. Such patient samples are typically placed in sample vials, extracted from the vials, combined with various reagents in special reaction cuvettes or tubes, incubated, and analyzed to aid in treatment of the patient. In typical clinical chemical analyses, one or two assay reagents are added at separate times to a liquid sample having a known concentration, the sample-reagent combination is mixed and incubated. Interrogating measurements, turbidimetric or fluorometric or absorption readings or the like are made to ascertain end-point or rate values from which an amount of analyte may be determined using well-known calibration techniques.

Although various known clinical analyzers for chemical, immunochemical and biological testing of samples are available, analytical clinical technology is challenged by increasing needs for improved levels of analysis. Due to increasing pressures on clinical laboratories to reduce cost-per-reportable result, there continues to be a need for improvements in the overall cost performance of automated clinical analyzers. In particular, sample analysis continuously needs to be more cost effective in terms of reducing consumables or increasing analyzer throughput for each and every reaction assay.

One contributor to reducing cost-per-reportable result is the ability to perform a large number of reaction assays in reaction cuvettes without requiring frequent operator intervention. It is therefore important that a large inventory of reaction cuvettes be maintained on automatic analyzers in such a manner that cuvettes may be automatically provided for performing reaction assays therein. In particular, the present invention provides a cuvette magazine having features to inventory cuvettes securely therein regardless of whether the magazine is positioned on the analyzer or removed therefrom.

SUMMARY OF THE INVENTION

The principal object of the invention is to provide a cuvette magazine for storing, transporting, and inventorying reaction cuvettes for use on an automated clinical analyzer. The cuvette magazine comprises a number of storage chutes sized to store a plurality of horizontally disposed reaction cuvettes therein and is aligned and secured within the analyzer by rails and tab features. The cuvette magazine further comprises a closure adapted to automatically open whenever the cuvette magazine is installed upon the analyzer thereby providing an opening through which reaction cuvettes may be moved unto the analyzer, the closure also adapted to automatically close whenever the cuvette magazine is removed from the analyzer so as to secure reaction cuvettes contained therein. The analyzer typically includes a circular rotatable assay reaction carousel for holding the assay reaction cuvettes and providing stepwise movements in a circular direction, the stepwise movements being separated by stationary dwell times, during which dwell time the wash station may conduct washing and drying operations so as to clean a reaction cuvette. An analyzer like those on which the present wash station may be used advantageously typically has a plurality of conventional assay operation stations at which are positioned individual assay devices, such as sensors, reagent add stations, mixing stations, separation stations, measuring stations and the like.

DETAILED DESCRIPTION OF THE INVENTION

Figure 1:
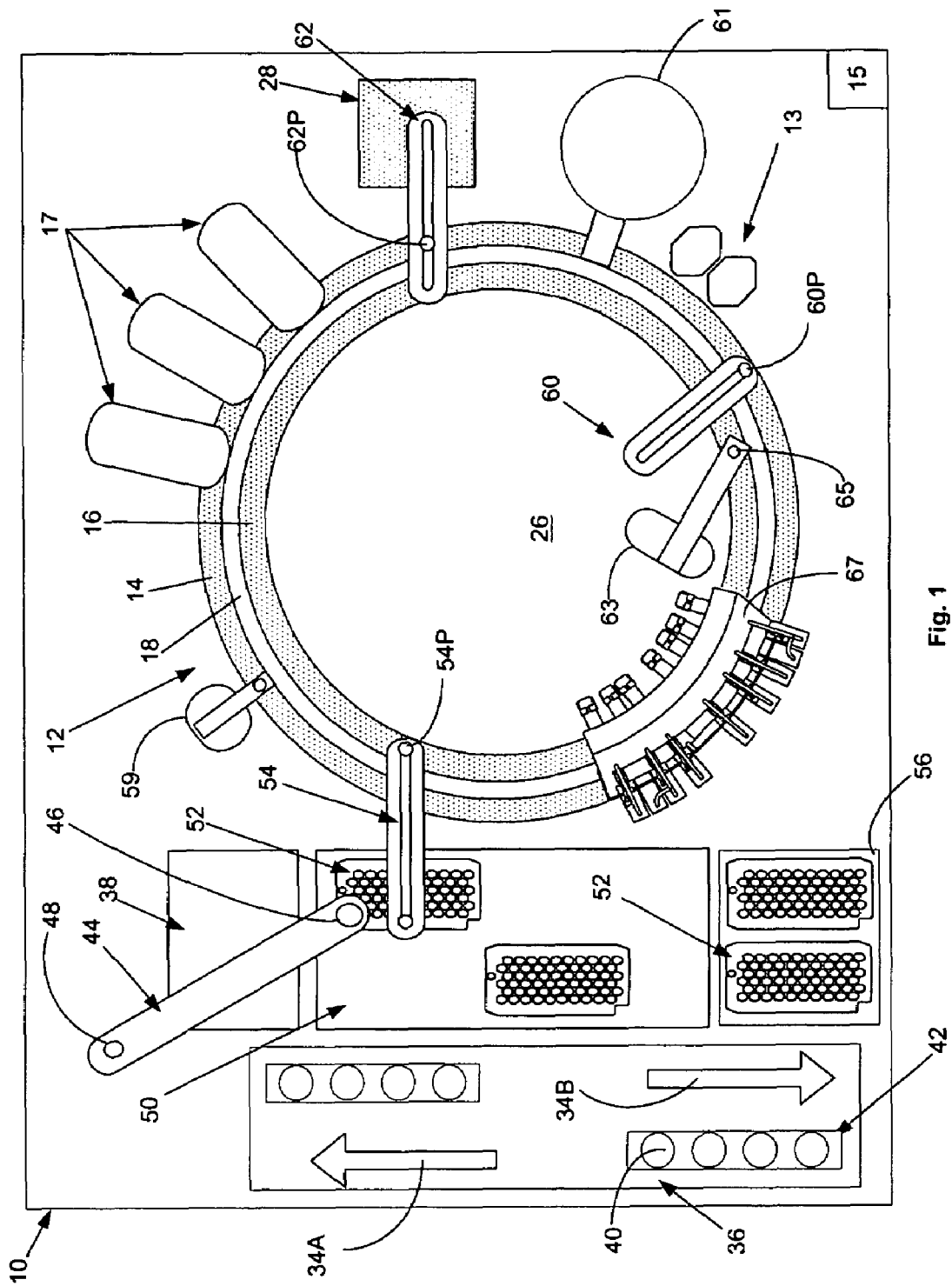
FIG. 1 is a schematic plan view of an automated analyzer in which the present invention may be employed to advantage.
Figure 2:
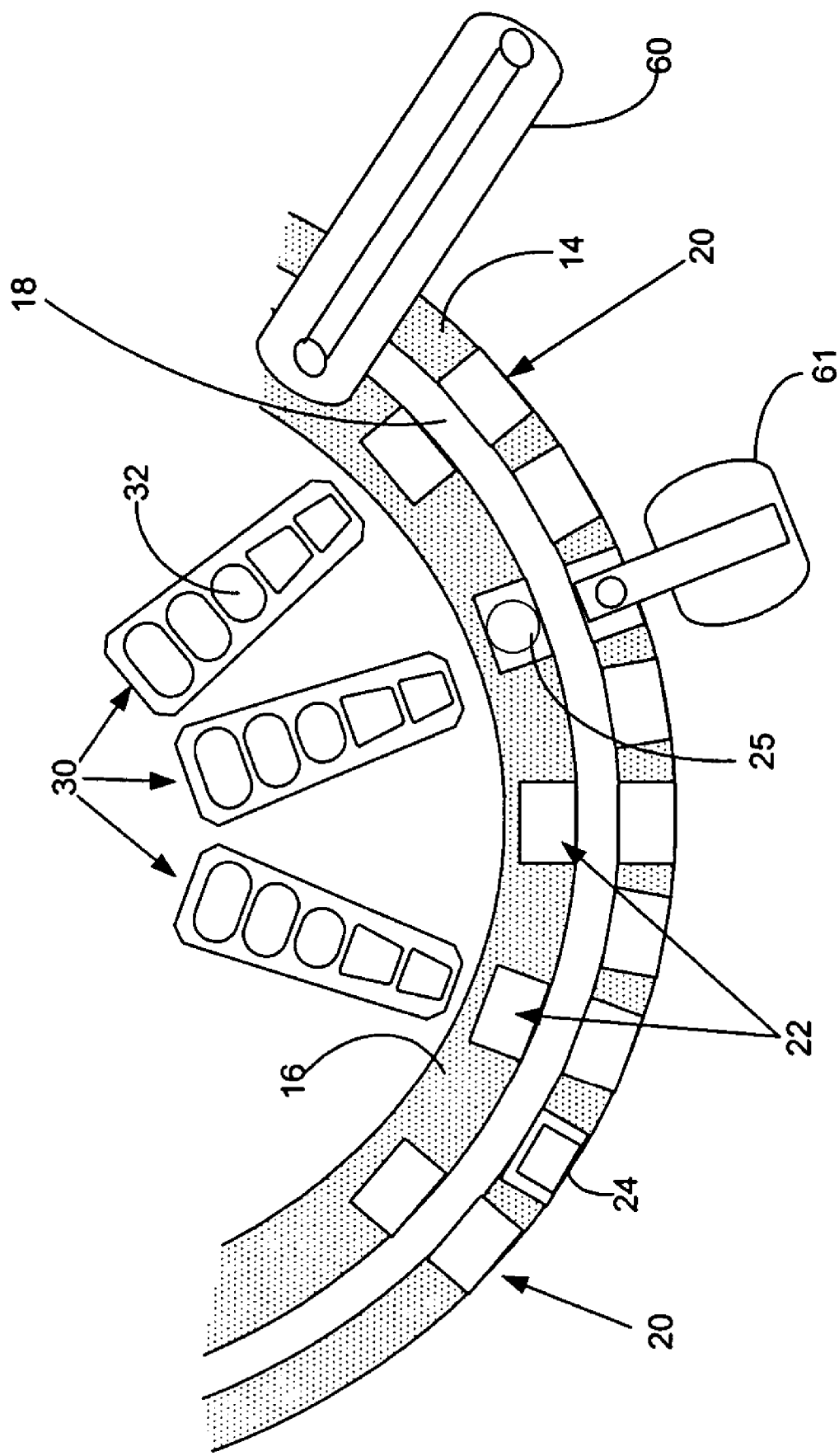
FIG. 2 is an enlarged schematic plan view of a portion of the analyzer of FIG. 1.

FIG. 1, taken with FIG. 2, shows schematically the elements of an automatic chemical analyzer 10 in which the present invention may be advantageously practiced, analyzer 10 comprising a reaction carousel 12 supporting an outer cuvette carousel 14 having cuvette ports 20 formed therein and an inner cuvette carousel 16 having vessel ports 22 formed therein, the outer cuvette carousel 14 and inner cuvette carousel 16 being separated by a open groove 18. Cuvette ports 20 are adapted to receive a plurality of reaction cuvettes 24 that contain various reagents and sample liquids for conventional clinical and immunoassay assays while vessel ports 22 are adapted to receive a plurality of reaction vessels 25 that contain specialized reagents for ultra-high sensitivity luminescent immunoassays. Reaction carousel 12 is rotatable using stepwise movements in a constant direction, the stepwise movements being separated by a constant dwell time during which carousel 12 is maintained stationary and computer controlled assay operational devices 13, such as sensors, reagent add stations, mixing stations and the like, operate as needed on an assay mixture contained within a cuvette 24.

Analyzer 10 is controlled by software executed by the computer 15 based on computer programs written in a machine language like that used on the Dimension® clinical chemistry analyzer sold by Dade Behring Inc, of Deerfield, Ill., and widely used by those skilled in the art of computer-based electromechanical control programming. Computer 15 also executes application software programs for performing assays conducted by various analyzing means 17 within analyzer 10.

Temperature-controlled reagent storage areas 26 and 28 store a plurality of multi-compartment elongate reagent cartridges 30 like that described in co-pending application Ser. No. 09/949,132 assigned to the assignee of the present invention, and containing reagents in wells 32 as necessary to perform a given assay.

A bi-directional incoming and outgoing sample tube transport system 36 having input lane 34A and output lane 34B transports incoming individual sample tubes 40 containing liquid specimens to be tested and mounted in sample tube racks 42 into the sampling arc of a liquid sampling arm 44. Liquid specimens contained in sample tubes 40 are identified by reading bar coded indicia placed thereon using a conventional bar code reader to determine, among other items, a patient's identity, the tests to be performed, if a sample aliquot is to be retained within analyzer 10 and if so, for what period of time. It is also common practice to place bar coded indicia on sample tube racks 42 and employ a large number of bar code readers installed throughout analyzer 10 to ascertain, control and track the location of sample tubes 40 and sample tube racks 42.

Figure 3:
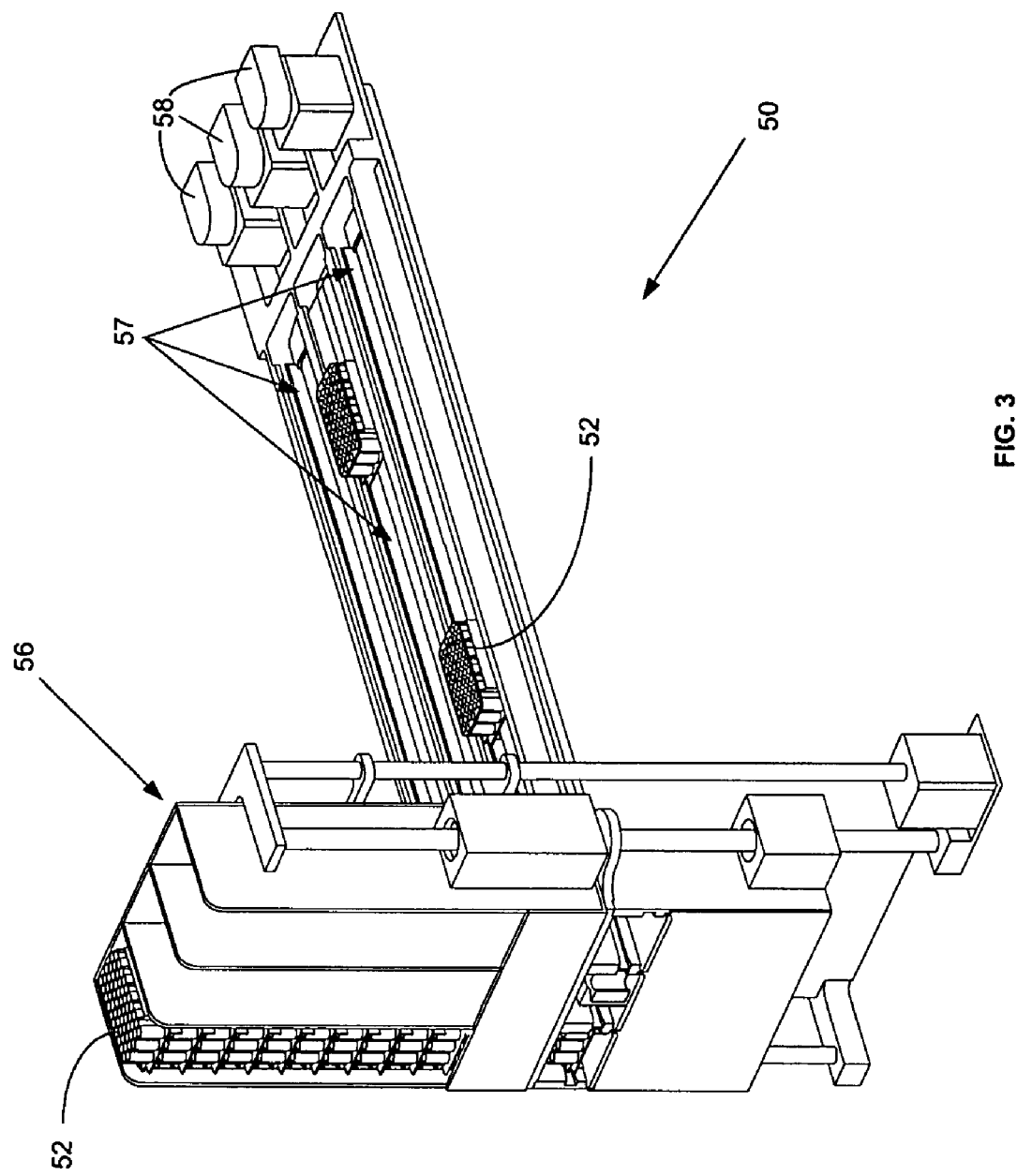
FIG. 3 is a perspective elevation view of an automated aliquot vessel array storage and handling unit that may be employed in the analyzer of FIG. 1.
Figure 4:
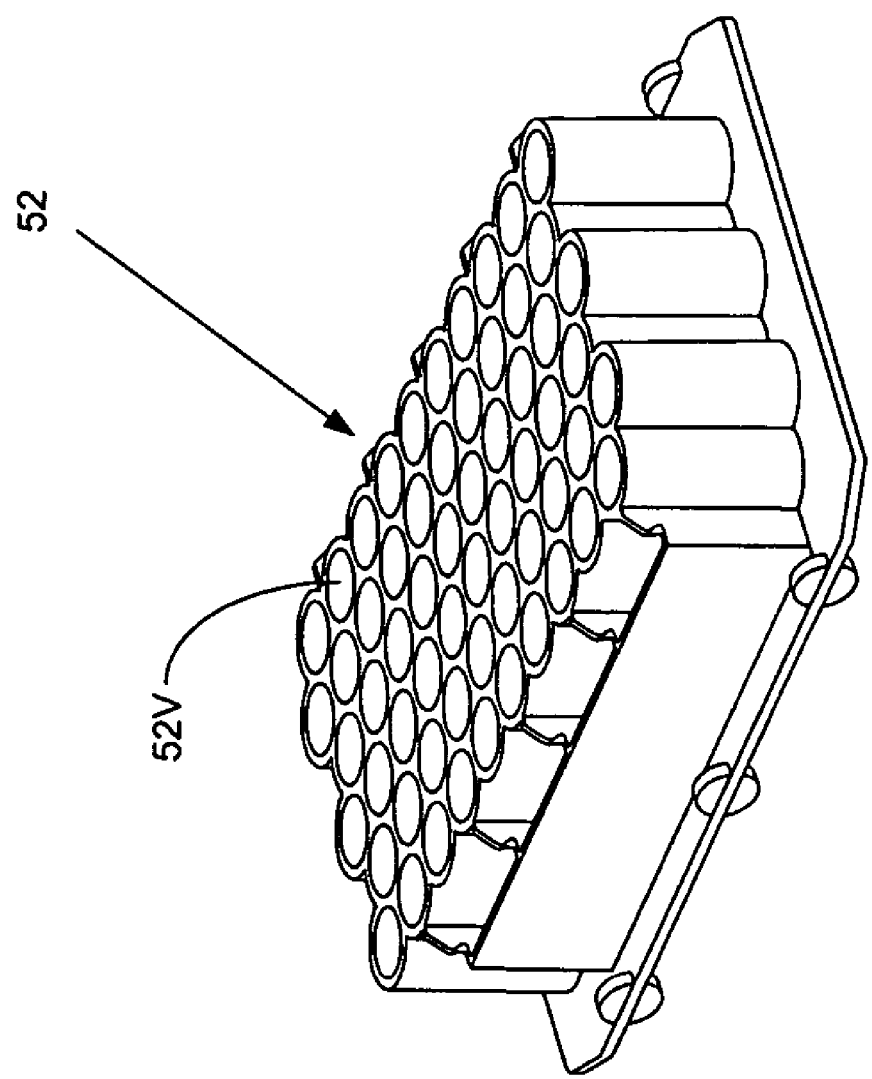
FIG. 4 is perspective elevation view of an aliquot vessel array that may be employed in the analyzer of FIG. 1.

Sampling arm 44 supports a liquid sampling probe 46 mounted to a rotatable shaft 48 so that movement of sampling arm 44 describes an arc intersecting the sample tube transport system 36 and an aliquot vessel array transport system 50, as seen in FIG. 3. Sampling arm 44 is operable to aspirate liquid sample from sample tubes 40 and to dispense an aliquot sample into one or more of a plurality of vessels 52V in aliquot vessel array 52, as seen in FIG. 4, depending on the quantity of sample required to perform the requisite assays and to provide for a sample aliquot to be retained by analyzer 10 within environmental chamber 38.

Aliquot vessel array transport system 50 comprises an aliquot vessel array storage and dispense module 56 and a number of linear drive motors 58 adapted to bi-directionally translate aliquot vessel arrays 52 within a number of aliquot vessel array tracks 57 below a sample aspiration and dispense arm 54 located proximate reaction carousel 12. Sample aspiration and dispense arm 54 is controlled by computer 15 and is adapted to aspirate a controlled amount of sample from individual vessels 52V positioned at a sampling location within a track 57 using a conventional liquid probe 54P and to then shuttle liquid probe 54P to a dispensing location where an appropriate amount of aspirated sample is dispensed into one or more cuvettes 24 in cuvette ports 20 for testing by analyzer 10 for one or more analytes. After sample has been dispensed into reaction cuvettes 24, conventional transfer means move aliquot vessel arrays 52 as required between aliquot vessel array transport system 50, environmental chamber 38 and a disposal area, not shown.

A number of reagent aspiration and dispense arms 60 and 62 comprising a pair of conventional liquid reagent probes, 60P and 62P, respectively, are independently mounted and translatable between reagent storage areas 26 and 28, respectively. Probes 60P and 62P comprise conventional mechanisms for aspirating reagents required to conduct specified assays at a reagenting location from wells 32 in an appropriate reagent cartridge 30, the probes 60P and 62P subsequently being shuttled to a reagent dispensing location where reagent (s) are dispensed into reaction cuvettes 24. A number of reagent cartridges 30 are inventoried in controlled environmental conditions inside reagent storage areas 26 and 28; a key factor in maintaining high assay throughput is the ability to quickly and accurately shuttle reagent cartridges 30 inside reagent storage areas 26 and 28 to reagenting locations for access by probes 60P and 62P.

Reaction cuvette load station 61 and reaction vessel load station 63 are respectively positioned proximate outer cuvette carousel 14 and inner vessel carousel 16 and are adapted to load reaction cuvettes 24 into cuvette ports 20 sideways as described later and reaction vessels 25 into vessel ports 22 using for example a sliding chute 65. In operation, used cuvettes 24 in which an assay has been finally conducted, are washed and dried in a wash station 67 like that described in patent publication number 2005-0014274, assigned to the assignee of the present invention. Subsequent assays are conducted in cleaned used cuvettes 24 unless dictated otherwise for reasons like disclosed in patent publication number 2004/0115095, assigned to the assignee of the present invention. Cuvette unload station 59 is adapted to remove unusable reaction cuvettes 24 from cuvette ports 20 again using a translatable robotic arm 65 like seen on load stations 61 and 63.

Figure 5:
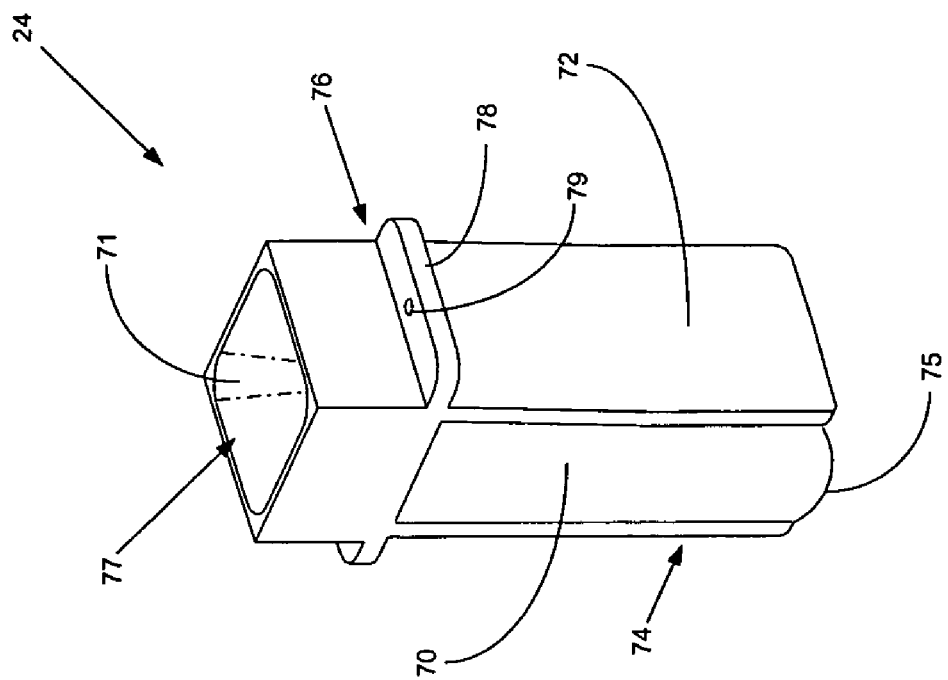
FIG. 5 is a perspective view of a typical reaction cuvette that may be employed in the analyzer of FIG. 1.

FIG. 5 is a external isometric view of reaction cuvette 24, like that described in patent publication number 2005-0013746, assigned to the assignee of the present invention, as having features to inhibit liquid wicking along an interior wall surface so that the presence of undesirable contaminants on the exterior surface of reaction cuvette 24 is minimized and the efficiency of washing by wash station 67 is increased. The reaction cuvette 24 shown in FIG. 5 may be formed as an essentially rectangular box-shaped part 24 with a mutually opposed front wall and back wall 70 perpendicular to and separating two mutually opposed side walls 72. A generally rectangular lower section 74 closed by a curved bottom surface 75 supports an open top section 76 with opening 77. A pair of projecting ledges 78 are formed on opposing sides of cuvette 24, each having a latching bulge 79 to facilitate automated handling formed therein. Anti-wicking fillets 71 are formed as a smooth transition that effectively blends the intersections of front and back walls 70 and side walls 72.

Figure 6:
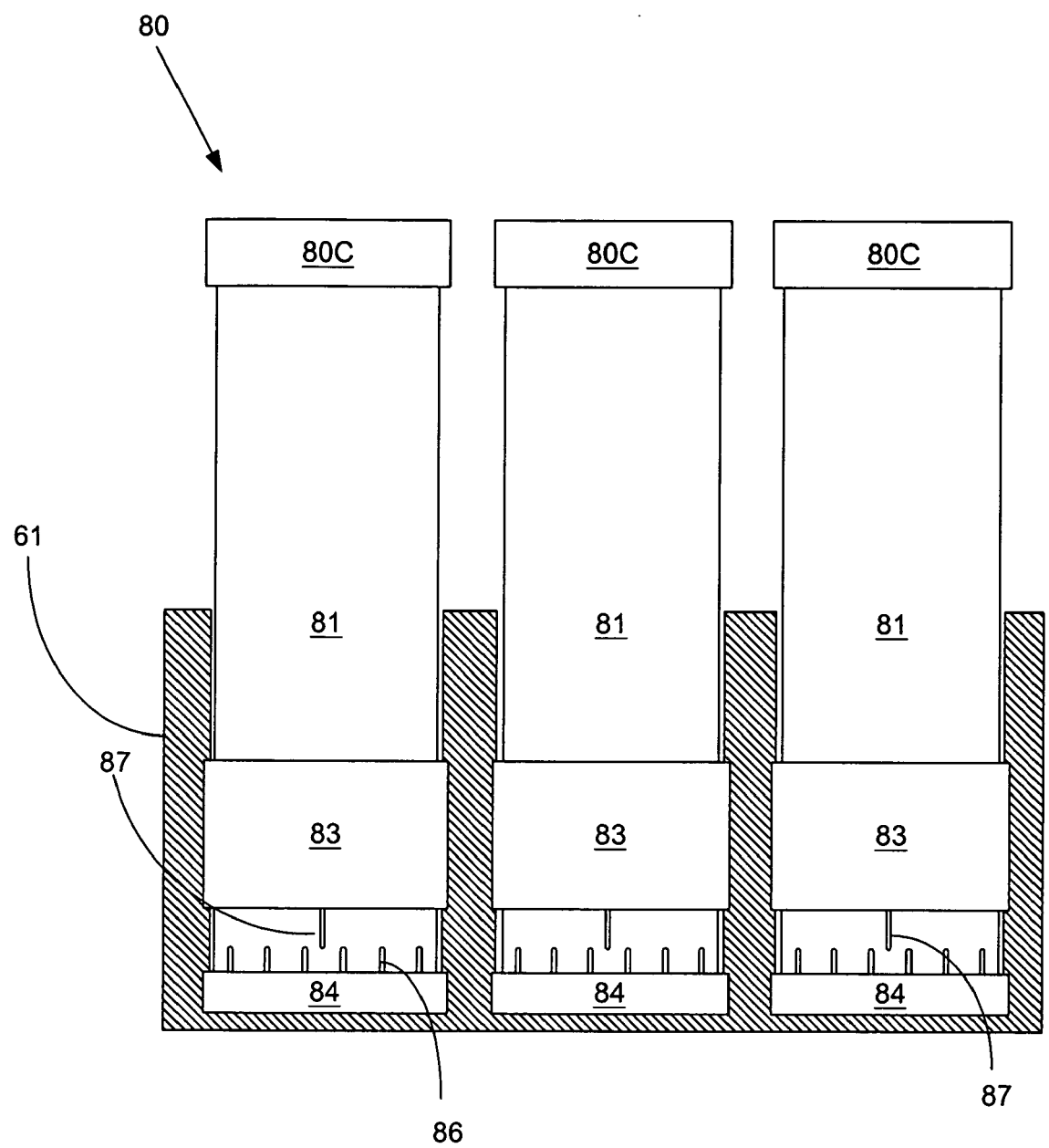
FIG. 6 is a front schematic elevation view of the cuvette magazine of the present invention.
Figure 7:
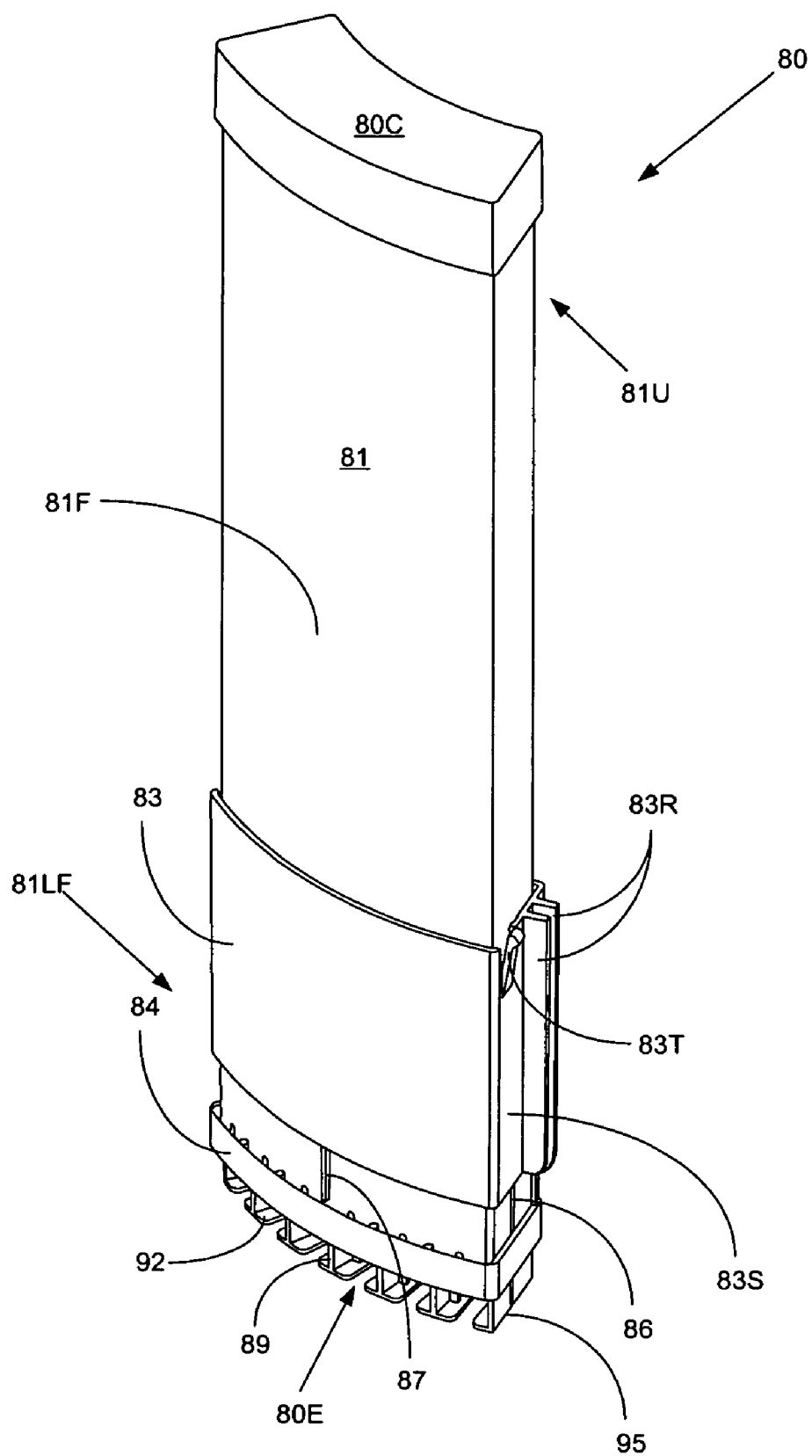
FIG. 7 is a front perspective view of the cuvette magazine of the present invention showing a sliding gate closure.
Figure 7A:
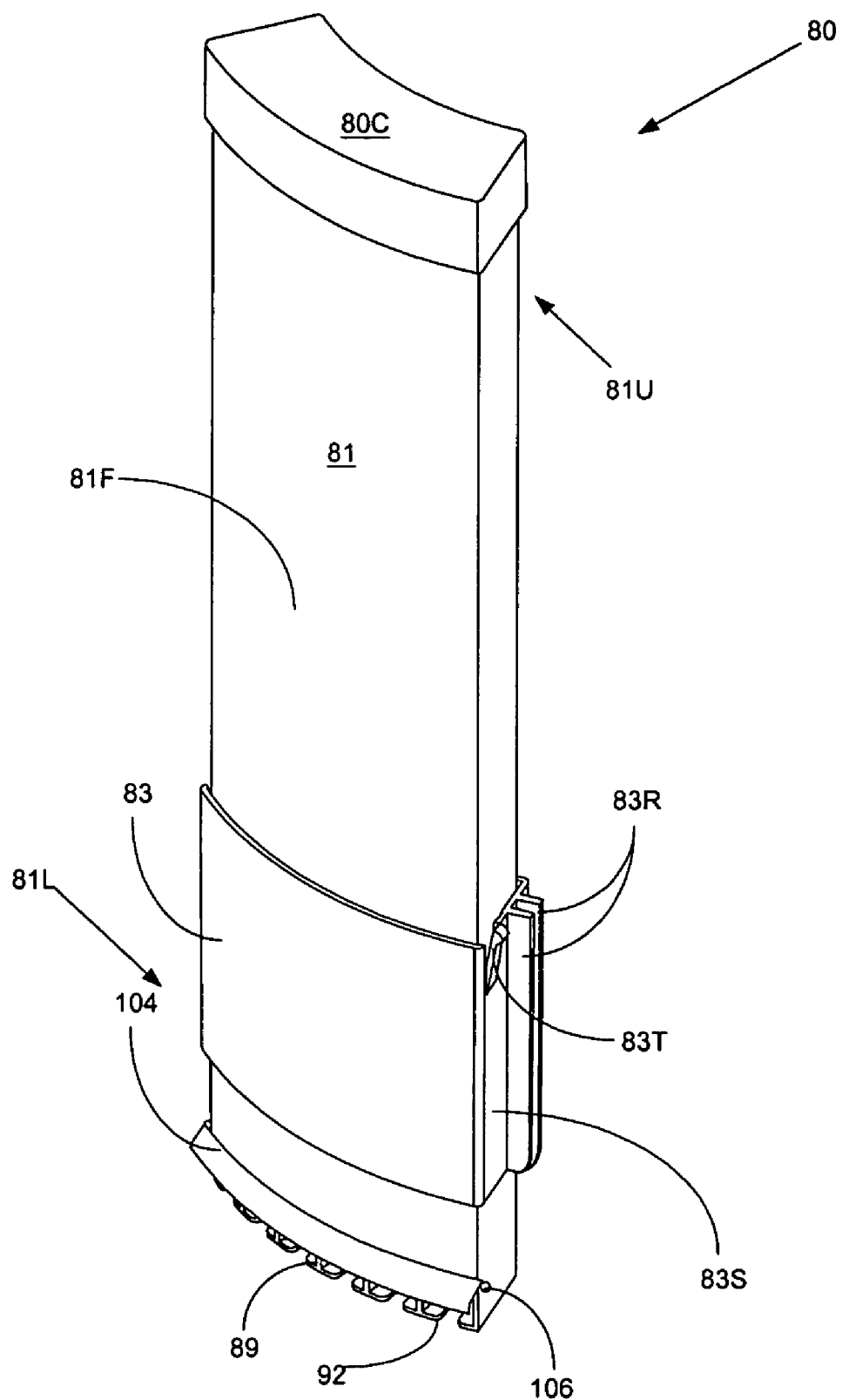
FIG. 7A is a front perspective view of the cuvette magazine of the present invention showing a hinged gate closure.
Figure 13:
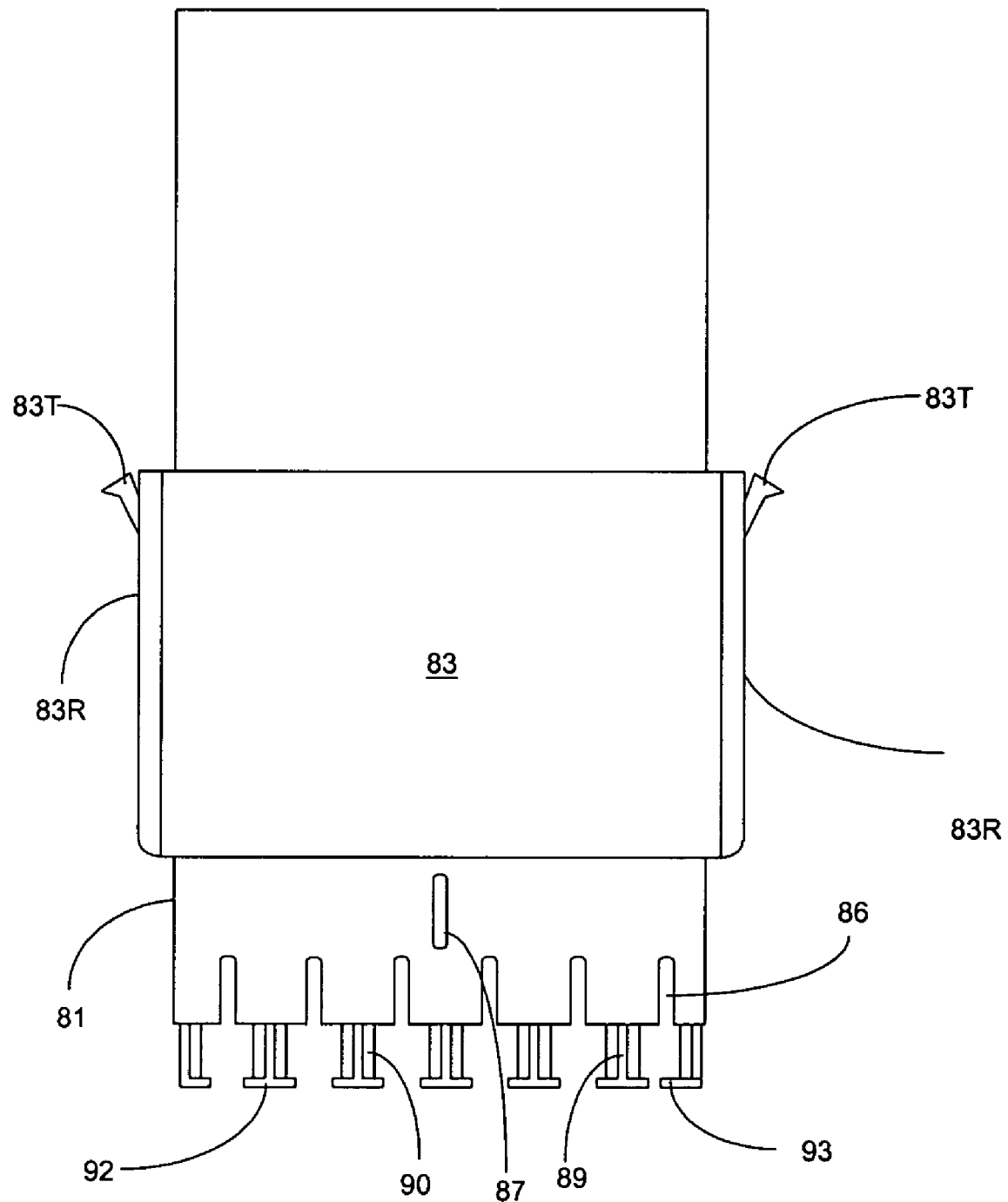
FIG. 13 is an enlarged front view of the foot section of the cuvette magazine of FIG. 7 with the sliding gate removed.
Figure 14:
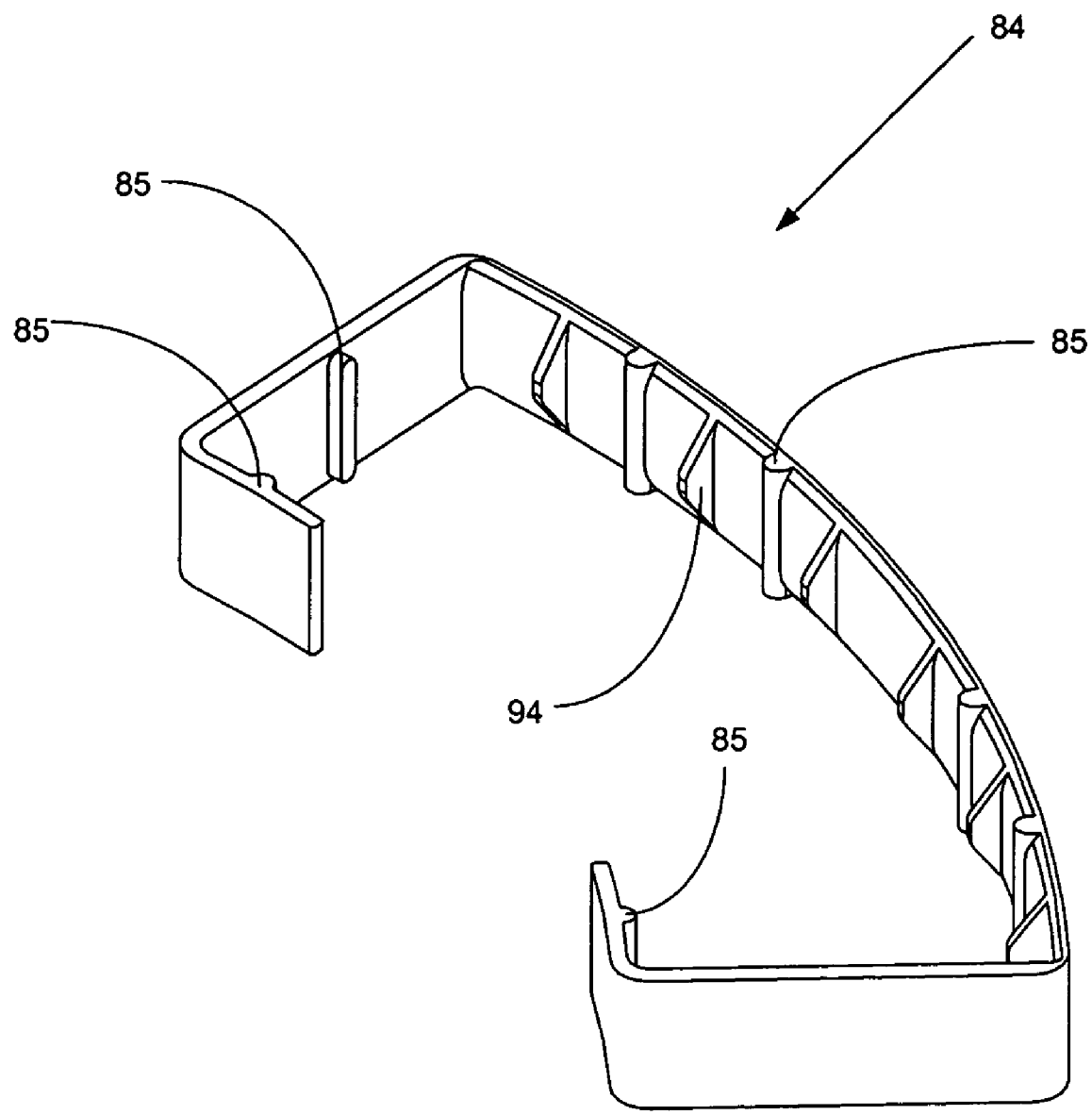
FIG. 14 is a perspective view of the sliding gate of FIG. 12.

The reaction cuvettes of FIG. 5 are typically molded of a hard plastic material and then automatically loaded into a cuvette magazine 80 like that seen in FIG. 6 and exemplary of the present invention. Cuvette magazine 80 comprises a curved, generally rectangular, storage cell 81 with an upper portion 81U and a lower portion 81L (best seen in FIGS. 7 and 8) with an integrated alignment and locking band 83 having two pairs of rails 83R and two locking tabs 83T formed on the exterior of storage cell 81 in the lower portion 81L. Rails 83R and locking tabs 83T are provided in order to vertically align cuvette magazine 80 and lock cuvette magazine 80 within respectively aligned grooves and recess within cuvette load station 61. A moveable closure 102 adapted to prevent reaction cuvettes 24 from sliding out of cuvette magazine 80 is located in the lower portion 81L. In one embodiment, moveable closure 102 comprises a vertically slideable gate 84 with a number of gate ribs 85 (best seen in FIG. 13) disposed within a corresponding number of open vertical slots 86, also in the lower front portion 81LF of storage cell 81 and on the two opposing sides 81S of storage cell 81 and on the bottom back 81BB of storage cell 81. A number of beveled gate notches 94 are also formed on the inner ribbed surface of gate 24 to meet a purpose explained later. A gate stop 87 is formed in the lower front portion 81LF a small distance above vertical slots 86 protruding slightly from storage cell 81 so as to stop the vertical displacement of gate 84 (FIG. 7). In an alternate embodiment, moveable closure 102 comprises a hinged gate 104 spring-loaded by hinge-spring 106 and adapted to swing outwards from a closed position preventing reaction cuvettes 24 from sliding out of cuvette magazine 80 to an opened position allowing reaction cuvettes 24 to be ejected from cuvette magazine 80 (FIG. 7A). In the instance of hinged gate 104 being employed, vertical slots 86 and gate stop 87 are unnecessary. A inclined ramp 103 formed in lower front portion 81LF automatically opens the hinged gate 104 when cuvette magazine 80 is installed on analyzer 10. Hinged gate 104 may be spring loaded so that it automatically closes when cuvette magazine 80 is removed from analyzer 10 to prevent reaction cuvettes 24 from sliding out of cuvette magazine 80. A removable cap 81C is sized to snugly cover the upper portion 81U, also to prevent reaction cuvettes 24 from sliding out of cuvette magazine 80.

Figure 9:
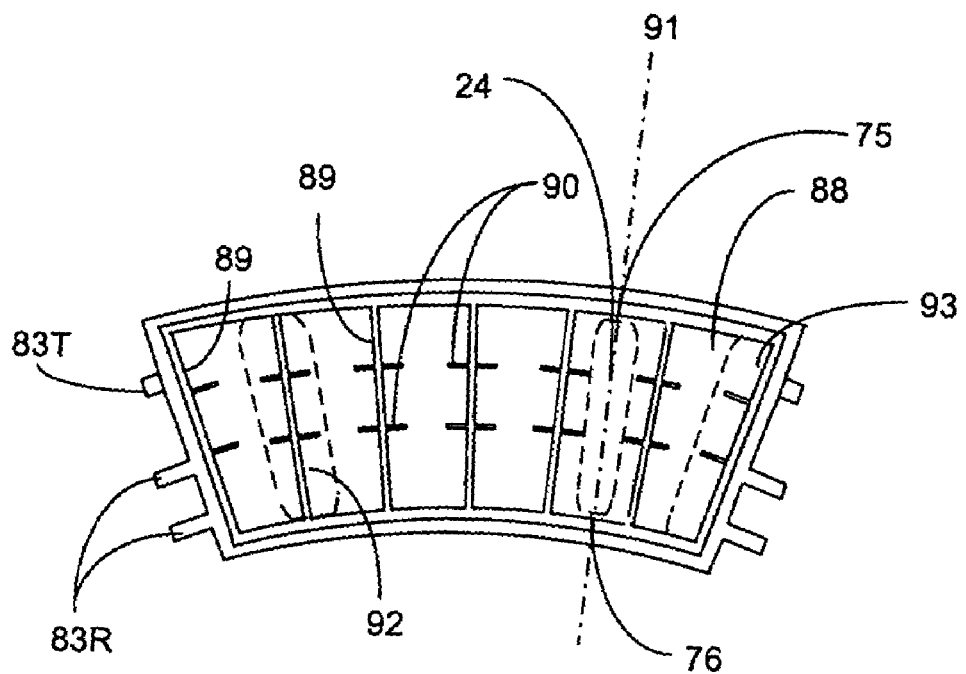
FIG. 9 is a top view of the cuvette magazine of FIG. 6.

As seen in the top view of cuvette magazine 80 in FIG. 9, having cap 81C removed, storage cell 81 is largely hollow except for a number of next adjacent storage chutes 88 enclosed by chute walls 89, each chute wall 89 having a two opposing pairs of ribs 90 protruding therefrom and into the interior space of each storage chute 88. For the purpose of illustration, a reaction cuvette 24 may be seen in dashed lines as disposed within a storage chute 88 and constrained in a horizontal orientation by the two opposing pairs of ribs 90. The primary purpose of cuvette magazine 80 is to hold a plurality of reaction cuvettes 24 stacked one upon another in each of the storage chutes 88 in a horizontal orientation, meaning that a line 91 drawn between curved bottom surface 75 and open top section 76 of reaction cuvette 24 is generally parallel to chute walls 89.

Figure 8:
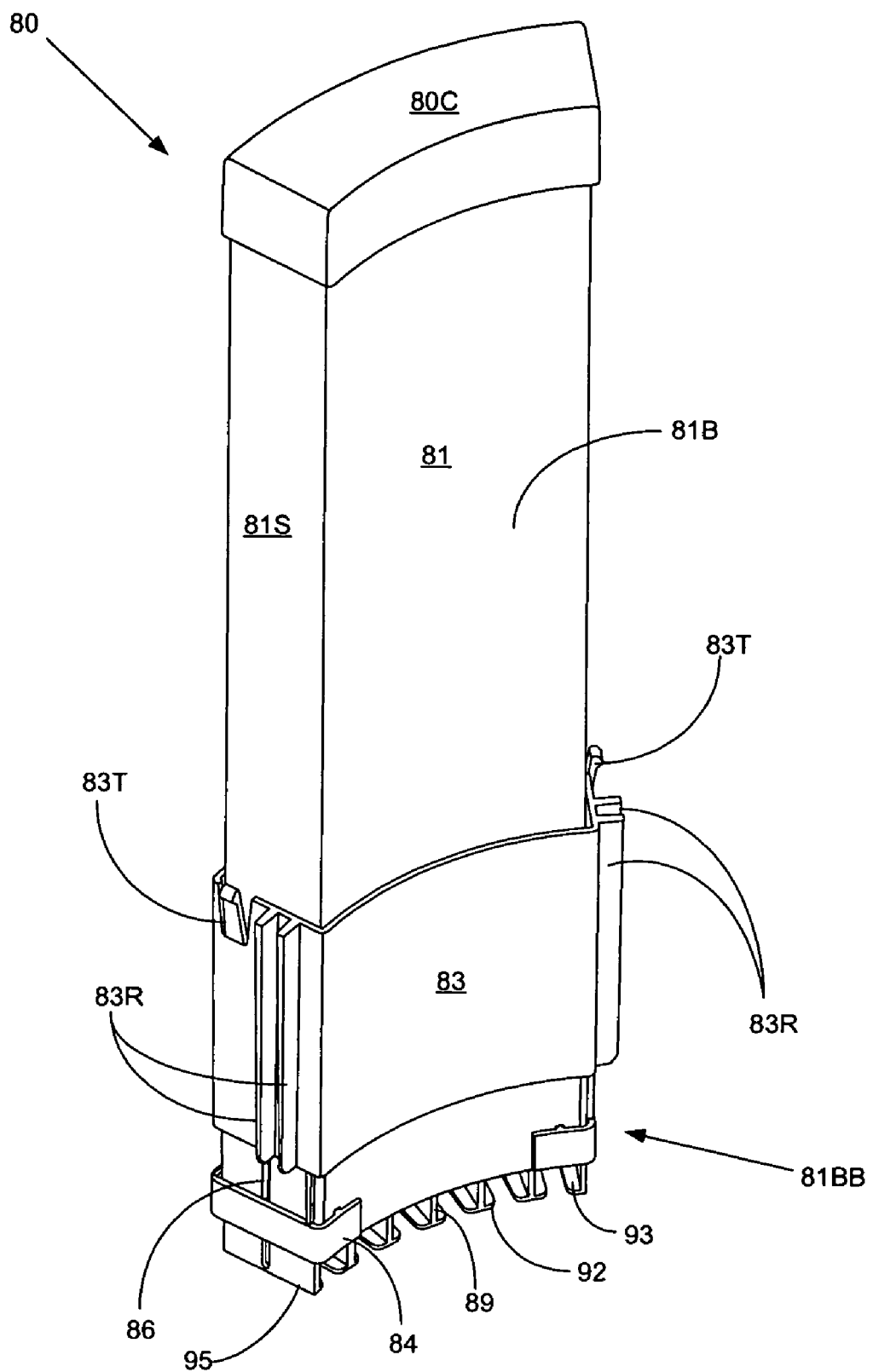
FIG. 8 is a back perspective view of the cuvette magazine of FIG. 7.
Figure 10:
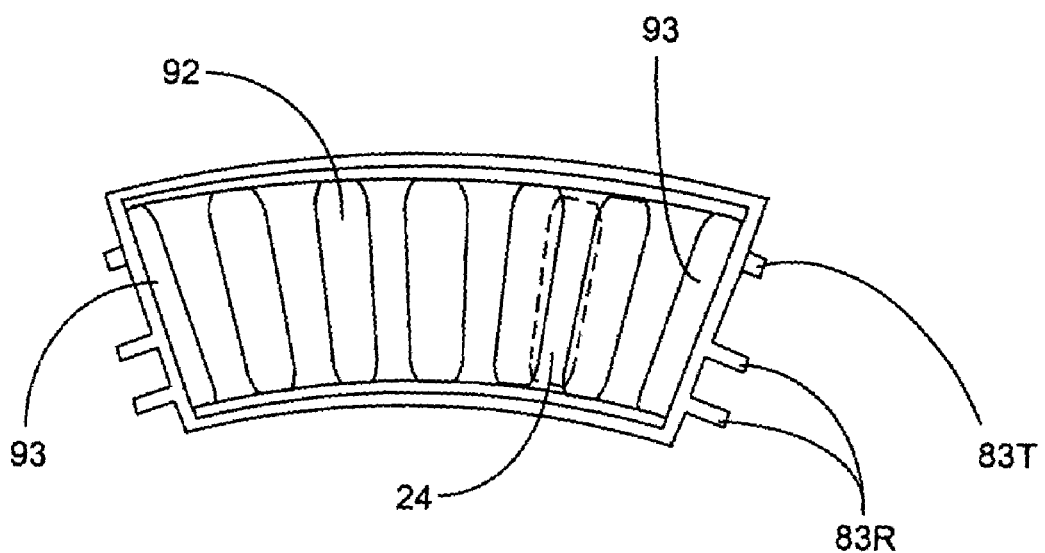
FIG. 10 is a bottom view of the cuvette magazine of FIG. 6.
Figure 11:
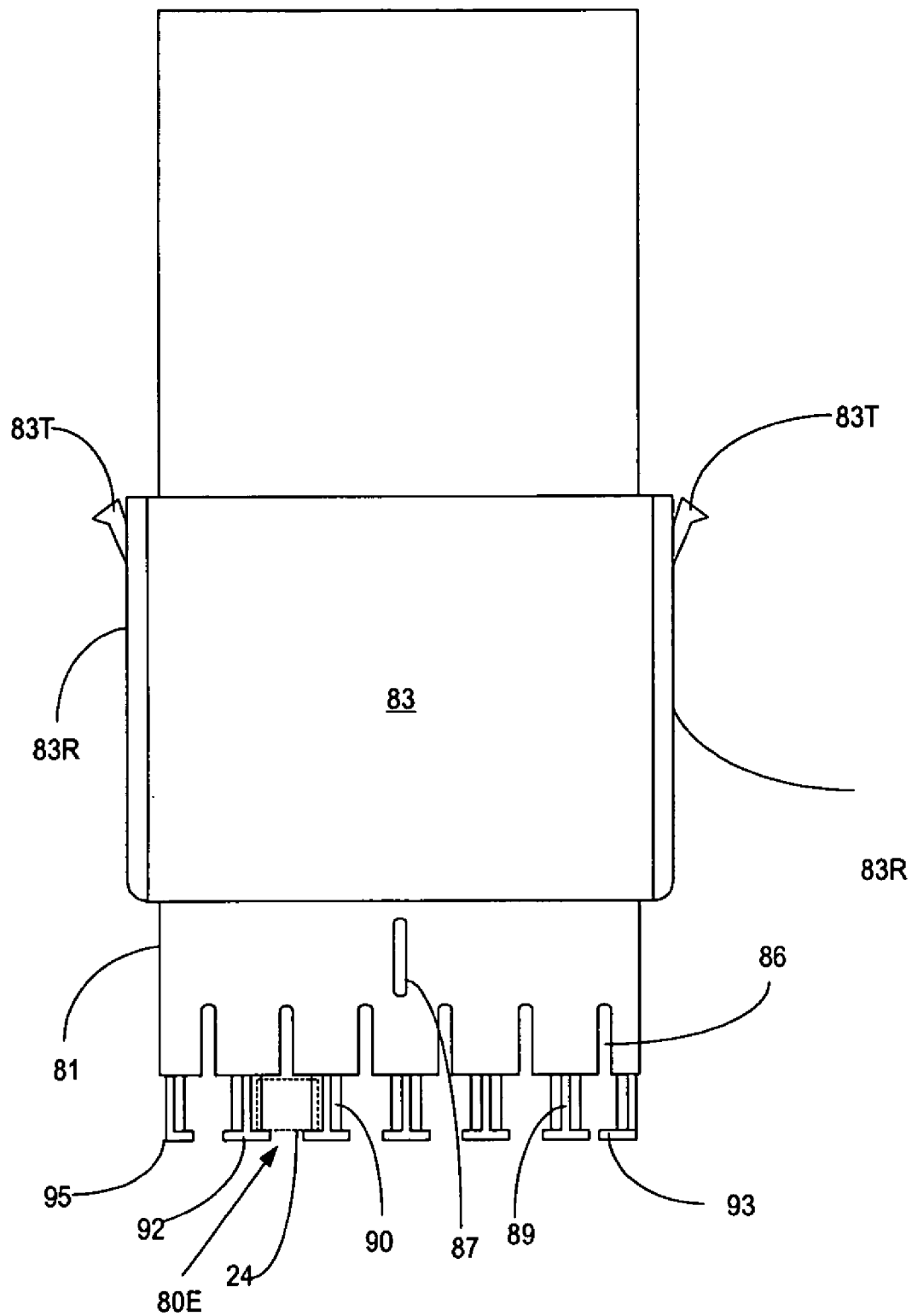
FIG. 11 is a front view of the cuvette magazine of FIG. 6 showing the reaction cuvette of FIG. 5 in a position to be ejected.
Figure 12:
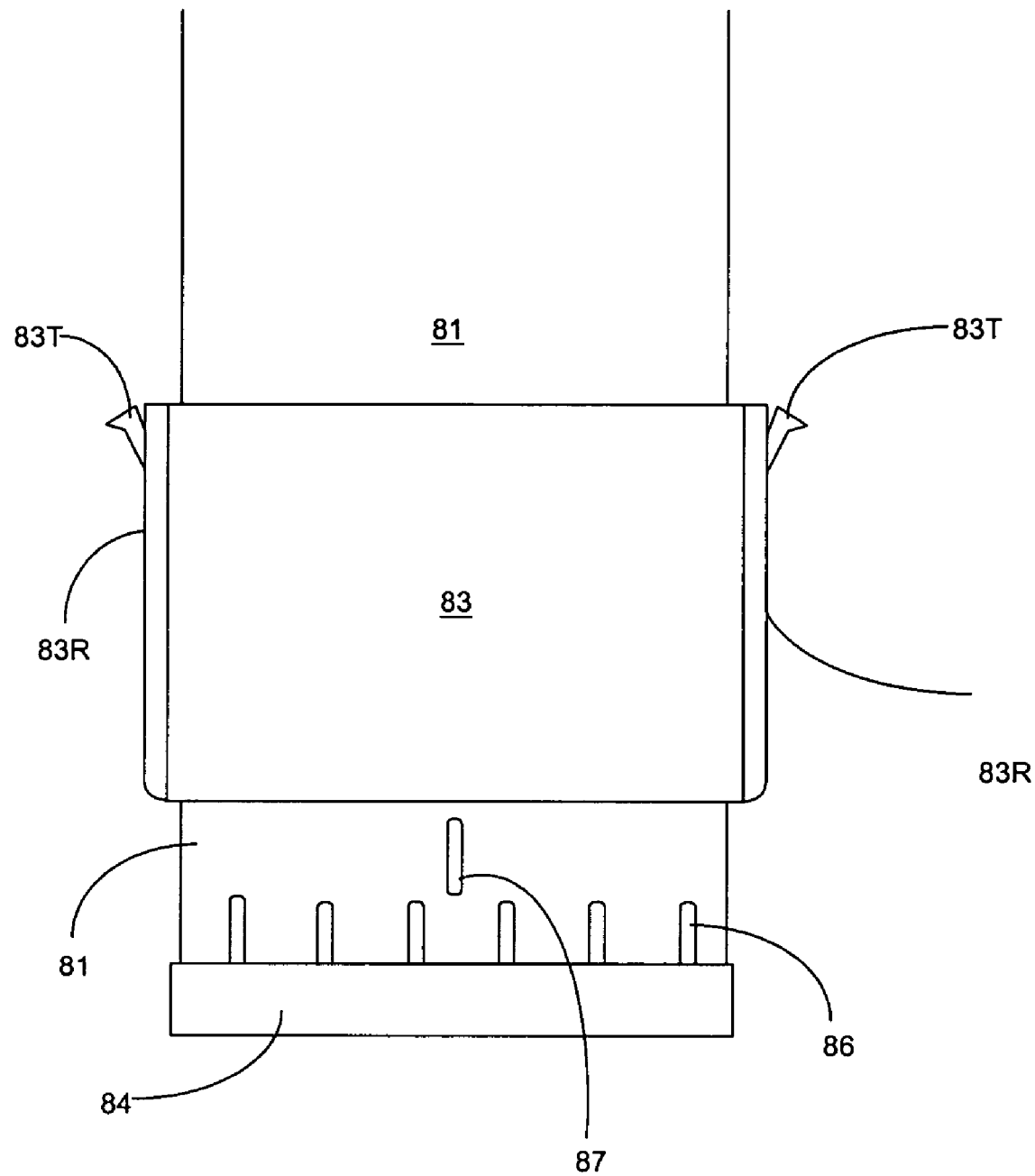
FIG. 12 is an enlarged front view of the foot section of the cuvette magazine of FIG. 7 with a closed sliding gate.

As seen in the bottom view of cuvette magazine 82 in FIG. 10, a flat pad 92 is formed at the lower extremity of each chute wall 89, except for the two chute walls 89 on the sides 81S of storage cell 81 where a flat ledge 93 about half the size of pad 90 protrudes therefrom and into the interior space of the respective two storage chutes 88. Again, a reaction cuvette 24 may also be seen in dashed lines as disposed within a storage chute 88 and prevented from falling out of storage chute 88 by flat pads 92 and flat ledges 93. Only a single flat pad 92 and flat ledge 93 are shown in dashed lines in FIG. 9 for purposes of simplicity in the drawing. As best seen in FIGS. 7, 8 and 11, the front and back curved surfaces 81F and 81B of storage cell 81 do not extend to the bottom 95 of cuvette magazine 80 so that a number of cuvette ejection openings 80E are formed at the front surface 81F between chute walls 89. FIG. 11 illustrates how a reaction cuvette 24, in dotted lines, may be held between two chute walls 89 and flat pads 92 and flat ledges 93, as well as illustrating how a reaction cuvette 24 may be freely displaced or ejected from cuvette magazine 80 through ejection openings 80E formed at front surface 81F.

Figure 15:
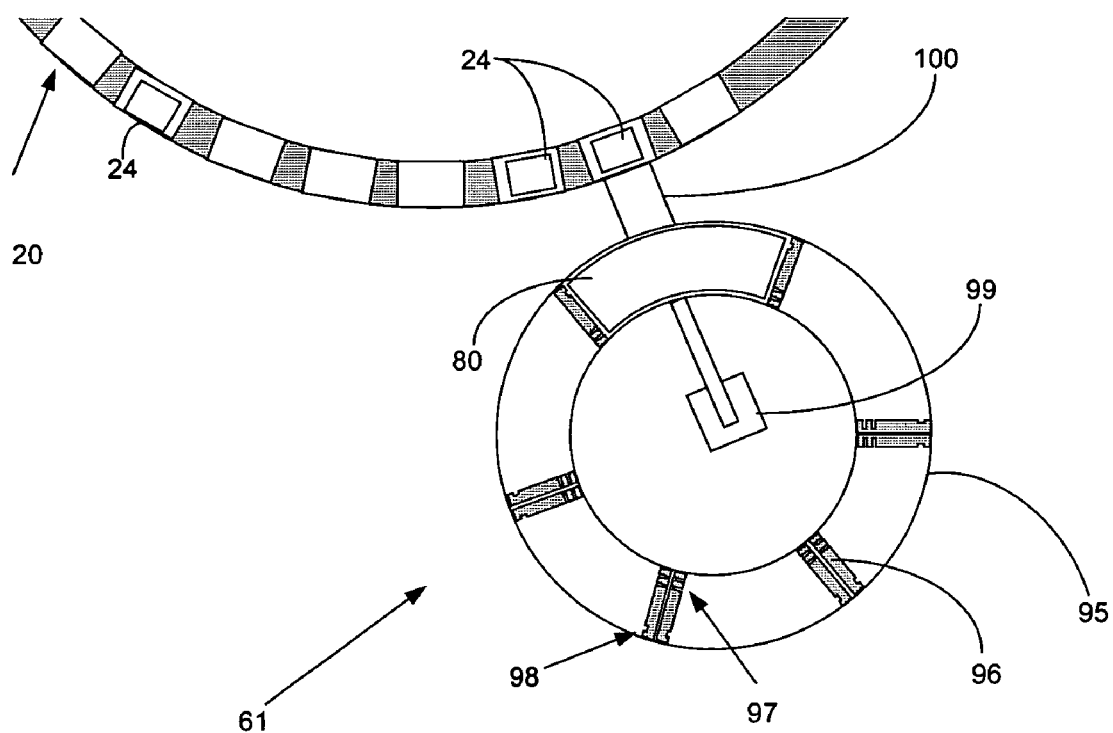
FIG. 15 is a top schematic view of a cuvette load station adapted for use with the cuvette magazine of FIG. 6.
Figure 16:
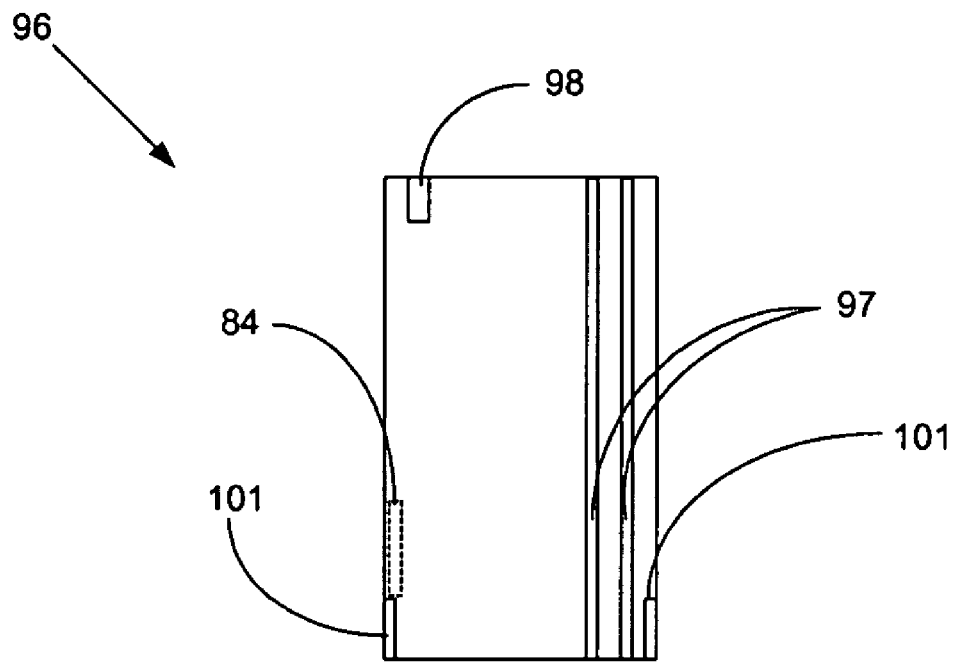
FIG. 16 is a side view of guide posts in the analyzer of FIG. 1. suitable for use with a sliding gate closure; and, FIG. 17 is a side view of guide posts in the analyzer of FIG. 1. suitable for use with a hinged gate closure.
Figure 17:
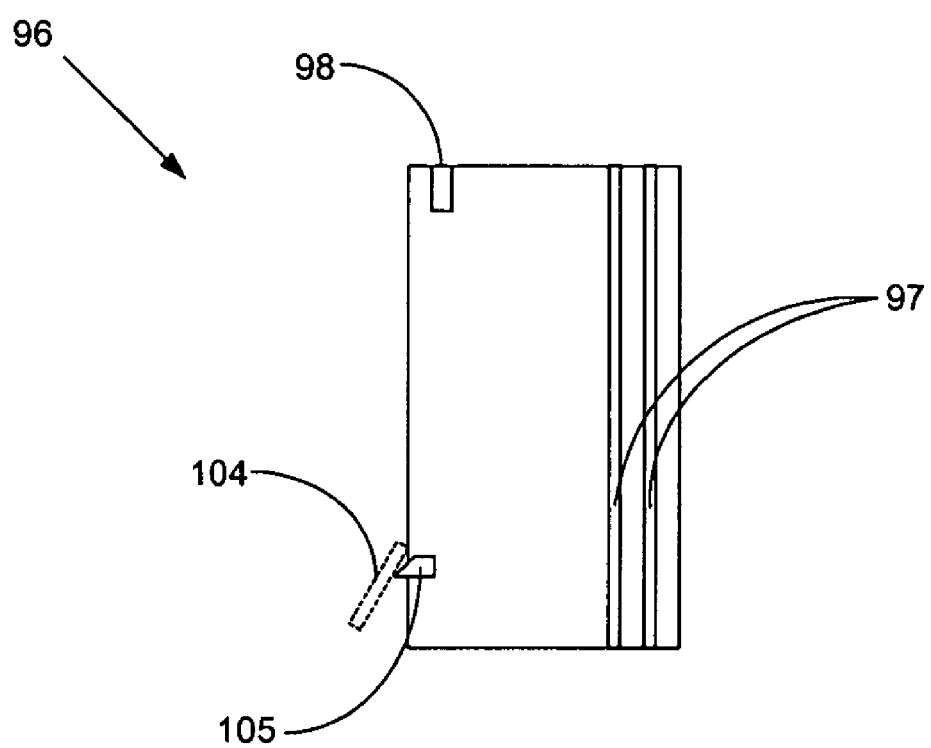

FIG. 15 illustrates cuvette loader 61 as comprising a circular rotatable turret 95 having a number of guide posts 96 spaced apart to receive a cuvette magazine 80 therebetween, guide posts 96 having notches 97 and a indent 98 formed on the sides thereof and dimensioned to interlock respectively with rails 83R and a locking tab 83T on the storage cell 81 of cuvette magazine 80. A pair of raised vertical ramparts 101, FIG. 16, are also formed on the sides of guide posts 96 so as to force slideable gate 84 upwards (as illustrated in dotted lines) when cuvette magazine 80 is inserted therebetween. Optionally, a biased tab may be included in turret 95 to assist in closing slideable gate 84 when cuvette magazine 80 is removed therefrom. In the embodiment in which moveable closure comprises hinged gate 104, as illustrated in dotted lines in FIG. 17, a single inclined ramp 105 is formed on each side of guide post 96 to force hinged gate 104 outwards (as illustrated in dotted lines) when cuvette magazine 80 is inserted therebetween. A linear actuator 99 is disposed within turret 95 and may be controlled by computer 15 to eject a cuvette 24 inventoried in a storage chute 88 out of cuvette magazine 80 through ejection openings 80E at the front surface 81F and into an open bottomed chute 100 sized such that gravitational pull causes the horizontally inventoried cuvette 24 to swing into a vertical orientation with open top section 76 of reaction cuvette 24 uppermost and drop into a cuvette port 20 in outer cuvette carousel 14. In the operation of analyzer 10, an operator inserts loaded cuvette magazines 80 onto turret 95, causing slideable gate 84 to move upwards or hinged gate 104 to swing outwards so that cuvettes 24 may be freely dispensed from storage chutes 88 into empty cuvette ports 20 as the outer carousel 14 rotates beneath chute 100. As described previously, gate ribs 85 on gate 84 are disposed within vertical slots 86 to facilitate the vertical sliding movement of gate 84. Locking tab 83T snaps into indent 98 to secure cuvette magazines 80 onto turret 95. If a partly filled cuvette magazine 80 is removed from turret 95, gate 84 slides downwards or hinged gate 104 closes to cover the ends of storage chutes 88, securing cuvettes 24 therein.

If a partly filled cuvette magazine 80 is removed from turret 95, it is possible that the rotational movement of turret 95 may have caused a cuvette 24 to be moved outwards by centrifugal forces acting thereon. In such an instance, an extruding portion of the cuvette 24 would likely interfere with the vertical sliding movement of gate 84. In order to prevent such an interference, beveled gate notches 86 are formed on the inner surface of gate 24 and extend inwards so that any such extruding cuvettes 24 are pushed back into storage chutes 88 as cuvette magazine 80 is removed from turret 95 and gate 84 is lowered. Clearly, the situation of outwardly moved cuvettes 24 is not an issue for hinged gate 104 since the closing motion will cause outwardly moved cuvettes 24 to be automatically pushed back into storage chutes 88 by the hinged gate 104 itself. The relative dimensions of items seen in FIG. 15 are not necessarily to scale and may be exaggerated for purposes of illustration.

The details of assembling a cuvette magazine 80 for use within an clinical analyzer is a task regularly encountered within the art and need not be described herein. It is sufficient that the teachings of the present invention, that a cuvette magazine advantageously includes features for being properly aligned and locked within the analyzer as well as features for automatically opening and closing to eject or retain cuvettes therein in order to enhance operation of the analyzer, be disclosed. For these reasons, the present invention is not limited to those embodiments precisely shown and described in the specification but only by the following claims.

We claim:

1. A magazine for releasably inventorying a plurality of reaction cuvettes to be used in an automatic clinical analyzer, the magazine comprising a generally rectangular storage cell having curved front and back surfaces between a top and a bottom, and a plurality of storage chutes therein, each chute sized to accommodate generally rectangular reaction cuvettes stacked one atop another therein, the storage chutes being defined by the front and back surfaces and a pair of opposing interior chute walls, each interior chute wall having two opposing pairs of ribs protruding therefrom and into the interior of each storage chute, wherein the front and back curved surfaces do not extend to the bottom of the magazine so that a number of cuvette ejection openings are formed at the front curved surface, and corresponding openings are formed on the back curved surface of the magazine between the chute walls.

2. The magazine of claim 1 wherein a flat pad is formed at the lower extremity of each interior chute wall protruding into the interior space of the storage chutes.

3. The magazine of claim 1 further comprising an alignment and locking band having two pairs of rails and two locking tabs formed on the exterior, upper portion thereof.

4. A magazine for releasably inventorying a plurality of reaction cuvettes to be used in an automatic clinical analyzer, the magazine comprising a generally rectangular storage cell having curved front and back surfaces between a top and a bottom, and a plurality of storage chutes therein, each chute sized to accommodate generally rectangular reaction cuvettes stacked one atop another therein, the storage chutes being defined by the front and back surfaces and a pair of opposing interior chute walls, each interior chute wall having two opposing pairs of ribs protruding therefrom and into the interior of each storage chute, the magazine further comprising a hinged gate proximate the bottom of the magazine, the gate spring-loaded by a hinge-spring on the curved front surface, the gate adapted to swing outwards from a closed position preventing reaction cuvettes from sliding out of the magazine to an opened position allowing reaction cuvettes to be ejected from the magazine.

* * * * *